(12) United States Patent
Maslowski

(10) Patent No.: US 11,554,142 B2
(45) Date of Patent: Jan. 17, 2023

(54) DOSAGE UNIT FORMULATIONS OF AUTOLOGOUS DERMAL FIBROBLASTS

(71) Applicant: Fibrocell Technologies, Inc., Exton, PA (US)

(72) Inventor: John M. Maslowski, Pottstown, PA (US)

(73) Assignee: Castle Creek Biosciences, LLC, Exton, PA (US)

(*) Notice: Subject to any disclaimer, the term of this patent is extended or adjusted under 35 U.S.C. 154(b) by 0 days.

(21) Appl. No.: 13/941,265

(22) Filed: Jul. 12, 2013

(65) Prior Publication Data

US 2013/0295061 A1 Nov. 7, 2013

Related U.S. Application Data

(63) Continuation of application No. 12/776,163, filed on May 7, 2010, now Pat. No. 8,529,883.

(51) Int. Cl.

| | | |
|---|---|---|
| *A61K 35/33* | (2015.01) | |
| *A61P 17/02* | (2006.01) | |
| *C12N 5/077* | (2010.01) | |
| *A61K 35/36* | (2015.01) | |
| *A61K 35/12* | (2015.01) | |

(52) U.S. Cl.
CPC .............. *A61K 35/33* (2013.01); *A61K 35/36* (2013.01); *A61P 17/02* (2018.01); *C12N 5/0656* (2013.01); *A61K 35/12* (2013.01)

(58) Field of Classification Search
CPC ..... A61K 35/33; A61K 90/0019; A61P 17/02; C12N 5/06; C12N 5/0656
See application file for complete search history.

(56) References Cited

U.S. PATENT DOCUMENTS

| | | | |
|---|---|---|---|
| 4,524,065 A | 6/1985 | Pinnell | |
| 4,772,557 A | 9/1988 | Eisen | |
| 5,591,444 A | 1/1997 | Boss, Jr. | |
| 5,660,850 A | 8/1997 | Boss, Jr. | |
| 5,665,372 A | 9/1997 | Boss, Jr. | |
| 5,858,390 A | 1/1999 | Boss, Jr. | |
| 6,110,459 A | 8/2000 | Mickle | |
| 6,432,710 B1 | 8/2002 | Boss, Jr. | |
| 6,733,530 B1 | 5/2004 | Lam | |
| 6,878,383 B2 | 4/2005 | Boss, Jr. | |
| 7,115,274 B2 | 10/2006 | Keller | |
| 7,186,557 B2 | 3/2007 | Marko | |
| 7,412,978 B1 | 8/2008 | Keller | |
| 7,767,452 B2 | 8/2010 | Kleinsek | |
| 7,799,325 B2 | 9/2010 | Kleinsek | |
| 8,529,883 B2 * | 9/2013 | Maslowski | 424/93.1 |
| 2002/0006649 A1 * | 1/2002 | Marx et al. | 435/174 |
| 2003/0228286 A2 * | 12/2003 | Boss et al. | 424/93.7 |
| 2004/0229203 A1 * | 11/2004 | Wiggins | A01N 1/0221 |
| | | | 435/1.1 |
| 2007/0264239 A1 * | 11/2007 | Huard | C12N 5/0657 |
| | | | 424/93.7 |
| 2007/0298005 A1 * | 12/2007 | Thibault | 424/70.31 |
| 2008/0015546 A1 * | 1/2008 | Casas et al. | 604/522 |
| 2008/0152628 A1 | 6/2008 | Kleinsek | |
| 2008/0199440 A1 * | 8/2008 | Leek | A61K 8/981 |
| | | | 424/93.7 |
| 2009/0017438 A1 * | 1/2009 | Roy et al. | 435/1.1 |
| 2009/0209456 A1 * | 8/2009 | Sweis | 514/9 |
| 2010/0256553 A1 * | 10/2010 | Fletcher | 604/28 |
| 2011/0110898 A1 | 5/2011 | Kleinsek | |

FOREIGN PATENT DOCUMENTS

| | | | |
|---|---|---|---|
| EP | 0845963 | 9/2003 | |
| JP | 2007528706 | 1/2005 | |
| JP | 2008-44950 | 2/2008 | |
| JP | 2008-245583 | 10/2008 | |
| JP | 2011-229413 A | 11/2011 | |
| WO | 04048557 | 6/2004 | |
| WO | 2007138269 | 12/2007 | |
| WO | 2008002064 | 1/2008 | |
| WO | WO 08/027984 | * | 3/2008 |

(Continued)

OTHER PUBLICATIONS

Boss et al, Annals Plastic Surg. 44(5):536-542, 2000.*
Han et al, Annals Plastic Surg. 56(3):251-255, 2006.*
McDaniel, J. Am. Acad. Dermatol. 58(2):AB136, 2008.*
Invitrogen, Biotechniques (November): p. 29 (protocol pp. 1-3), 2009.*
Van den Bogaerdt et al, Arch. Dermatol. Res. 294:135-142, 2002.*
Chhetri et al, Otolaryngol. Head Neck Surg. 131:864-870, 2004.*
Mansbridge et al, Tissue Engineering 4(4):403-414, 1998.*
Watson et al, Arch Facial Plast. Surg. 1:165-170, 1999.*
Smith et al, J. Am. Acad. Dermatol. 58(2): P2810, p. AB138, Feb. 2008.*
Fibrocell Technologies, Inc. CTGTAC Briefing Document, FDA Report, Advisory Committee Briefing Materials available for public release, Sep. 9, 2009.*
Baust et al, Organogenesis 5(3): 90-96, available online Jul. 1, 2009.*
Baust et al, Cryobiol. 45: 97-108, 2002.*

(Continued)

*Primary Examiner* — Kevin K Hill
(74) *Attorney, Agent, or Firm* — Armstrong Teasdale LLP

(57) ABSTRACT

Dosage units consist of an autologous cell therapy product composed of fibroblasts grown for each individual to be treated. The suspension of autologous fibroblasts, grown from a biopsy of each individual's own skin using current good manufacturing practices (CGMP), and standard tissue culture procedures, is supplied in vials containing cryopreserved fibroblasts or precursors thereof, having a purity of at least 98% fibroblasts and a viability of at least 85%, for administration of from one to six mL, preferably two mL, of cells at a concentration of from $1.0\text{-}2.0 \times 10^7$ cells/mL. When injected into the nasolabial fold wrinkles (creases on the sides of the nose that extend to the corners of the mouth), the autologous fibroblasts are thought to increase the synthesis of extracellular matrix components, including collagen, reducing the severity of these wrinkles. Dosage and timing of administration have been demonstrated to be critical to achieving clinically significant outcomes.

7 Claims, 6 Drawing Sheets

(56) References Cited

FOREIGN PATENT DOCUMENTS

| WO | WO2008027984 | 3/2008 |
| WO | 2008/081818 | 7/2008 |
| WO | 2008083223 | 7/2008 |
| WO | 2009023161 | 2/2009 |
| WO | 2009142717 | 11/2009 |
| WO | 2009/156398 | 12/2009 |
| WO | 2010008486 | 1/2010 |

OTHER PUBLICATIONS

Murakawa et al, J. Thorac. Cardiovasc. Surg. 120: 712-719, 2000.*

Wang et al, Cryobiology 55: 60-65, 2007.*

Ghahary, et al., "Collagenase production is lower in post-burn hypertrophic scar fibroblasts than in normal fibroblasts and is reduced by insulin-like growth factor-1", J. Invest Dermal., 106(3):46-81 (1996).

Watson, et al., "Autologous fibroblasts for treatment of facial rhytids and dermal depressions. A pilot study", Arch. Facial Plast. Surg., 1:165-70 (1999).

Lee et al., A new dermal equivalent: the use of dermal fibroblast culture alone without exogenous materials, J Derm Sci 2006 43:95-104.

Kubo and Kuroyanagi, Development of a cultured dermal substitute composed of a spongy matrix of hyaluronic acid and atelo-collagen combined with fibroblasts: cyropreservation, Artifical Organs 2004 28(2):187-188.

Weiss, R. et al., "Autologous Cultured Fibroblast Injection For Facial Contour Deformities: A Prospective, Placebo-Controlled, Phase III Clinical Trial", Dermatologic Surgery, 2007, 33:263-268.

Boss, et al., "Autologous cultured fibroblasts as cellular therapy in plastic surgery", Clinical Plastic Surgery, 27:613-626 (2000).

Byrne, et al., "Generation of isogenic pluripotent stem cells", Hum. Mol. Gen., 17:R37-R41 (2008).

Byrne, et al.,"Producing primate embryonic stem cells by somatic cell nuclear transfer", Nature, 450(7169):497-502 (2007).

Cohen and Holmes, "Artecoll: a long-lasting injectable wrinkle filler material: Report of a controlled, randomized, multicenter clinical trial of 251 subjects", Plast Reconstr Surg., 114(4):964-76 (2004).

Cowan, et al., "Nuclear reprogramming of somatic cells after fusion with human embryonic stem cells", Science, 309(5739):1369-73 (2005).

Delustro, et al., "Reaction to injectable collagen: results in animal models and clinical use" , Plastic and Reconstructive Surgery, 79:581 (1987).

Hochedlinger, et al., "Epigenetic reprogramming and induced pluripotency", Development, 136(4):509-23 (2009.

Iwuagwu, "The use of skin grafts in postburn contracture release: a 10-year review", Plast Reconstr Surg., 103(4):1198-204 (2004).

Kanawaty, et al., "Genomic analysis of induced pluripotent stem (iPS) cells: routes to reprogramming", Bioessays, 31(2):134-8 (2009).

Lemperle, et al., "A classification of facial wrinkles", Plast Reconstr Surg., 108(6):1735-50 (2001).

Sparman, et al., "Epigenetic reprogramming by somatic cell nuclear transfer in primates" , Stem Cells, 27(6):1255-64 (2009).

Takahashi, et al., Induction of pluripotent stem cells from adult human fibroblasts by defined factors, Cell, 131(5):861-72 (2007).

International Search Report for PCT/US2011/035332 dated Sep. 1, 2011.

Cell Biology and Cell Engineering Experimental Course, Zhu, et al. Northeast Forestry University Press, 1st Edition, Sep. 30, 2006, p. 184-193.

Cell Culture, Szeto, Z.Q., et al., World Publishing Xian Company, Jan. 2007, 2nd Edition, First Printing, p. 4.

Clinical Flow Cytometry Laboratory Technology Wu Lijuan, et al., People's Military Medical Publishing House, Aug. 2010, 1st edition 1st printing, p. 4.

* cited by examiner

DOSAGE UNIT FORMULATIONS OF AUTOLOGOUS DERMAL FIBROBLASTS

CROSS REFERENCE TO RELATED APPLICATIONS

The present application is a continuation of U.S. Ser. No. 12/776,163, filed May 7, 2010, entitled "Dosage Unite Formulations of Autologous Dermal Fibroblasts", by John M. Maslowski, all of which are herein incorporated in their entirety by reference.

FIELD OF THE INVENTION

This relates to dosage unit formulations of isolated, prepared autologous dermal fibroblasts for injection at a site for the repair and/or long term augmentation of skin and soft tissue defects in human subjects.

BACKGROUND OF THE INVENTION

As described in U.S. Pat. Nos. 5,591,444, 5,660,850, 5,665,372, and 5,858,390, cosmetic and aesthetic defects in the skin of a subject can be corrected by the injection of a suspension of autologous dermal fibroblasts into the dermis and subcutaneous tissue subadjacent to the defect. Typical defects that can be corrected by this method include rhytids, stretch marks, depressed scars, cutaneous depressions of non-traumatic origin, scaring from acne vulgaris, and hypoplasia of the lip. The cells are histocompatible with the subject, preferably derived by culture of a biopsy specimen taken from the subject, and have been expanded by passage in a cell culture system.

The injection of a material (an "injectate") into the body, and particularly into the face, to create an aesthetic result dates to the close of the nineteenth century. For example, the injection of paraffin to correct facial contour defects enjoyed a brief period of acceptance in the years prior to World War I. However, complications and the unsatisfactory nature of the long-term results caused the practice to be abandoned. The availability of injectable silicone gave rise to a virtual repetition of these events beginning in the early 1960s. Specially manufactured "medical grade" silicone solutions, e.g., Dow Corning MDX 4.4011, have been used on an experimental basis in a number of approved test centers in the United States. Complications, such as local and systemic reactions to the silicone, migration of the injectate, and local tissue break down, have limited the use of silicone injections. The poor results obtained by the injection of non-biological materials prompted attempts to use foreign proteins, particularly bovine collagen, as an injectate. Although unprocessed bovine collagen is too immunogenic for injection into humans, the removal by enzymatic degradation of C- and N-terminal peptides of bovine collagen yields a material ("atelocollagen") that can be used in limited quantities if patients are pre-screened to exclude those patients who are immunoreactive. Although used widely, the material was associated with the development of anti-bovine antibodies in about 90% of subjects and with overt immunologic complications in about 1-3% of subjects. DeLustro, F., et al., 1987, Plastic and Reconstructive Surgery 79:581. Atelocollagen in solution proved to be less than completely satisfactory because the material was absorbed in a relatively short time by the subject from the site of injection without replacement by host material. Residence in the body was increased by glutaraldehyde cross-linking, followed by filtration and shearing by passage through fine mesh. The increased and irregular viscosity rendered the material too difficult to use, however. Human collagen for injection that is derived entirely from a sample of the subjects own tissue is available but there is no evidence that human collagen injections are any more persistent than bovine collagen injections.

These problems were overcome through the development of the autologous fibroblast preparations. However, having a solution to a problem is not the same as having a product which is stable to store in defined dosages that have been validated by trial and error and confirmed by clinical trials, and which have been manufactured and packaged in compliance with the requirements of the U.S. Food and Drug Administration.

It is therefore an object of the present invention to provide defined dosage unit formulations of autologous dermal fibroblasts for injection into patients for the repair and long term augmentation of skin defects.

It is a further object of the present invention to provide dosage unit formulation that contain stem cells, precursor cells or partially differentiated cells that can be used for the repair and long term augmentation of skin defects.

SUMMARY OF THE INVENTION

Dosage units consist of an autologous cell therapy product composed of fibroblasts grown for each individual to be treated. The suspension of autologous fibroblasts, grown from a biopsy of each individual's own skin using current good manufacturing practices (CGMP) and standard tissue culture procedures, is supplied in vials containing cryopreserved fibroblasts or precursors thereof, having a purity of at least 98% fibroblasts and a viability of at least 85%, for administration of from one to six mL, preferably two mL administered three times approximately five weeks apart, of cells at a concentration of from $1.0$-$2.0 \times 10^7$ cells/mL, injected to between 0.05 and 0.5 mL per linear centimeter. The passaged dermal fibroblasts are rendered substantially free of immunogenic proteins present in the culture medium by incubating the expanded fibroblasts for a period of time in protein free medium. When injected into the nasolabial fold wrinkles (creases on the sides of the nose that extend to the corners of the mouth), the autologous fibroblasts are thought to increase the synthesis of extracellular matrix components, including collagen, reducing the severity of these wrinkles. Dosage and timing of administration have been demonstrated to be critical to achieving clinically significant outcomes.

Although there are several approved therapies in the United States (US) for the treatment of nasolabial fold wrinkles, such as Restylane®, Juvéderm™ and Radiesse®, the fibroblast cell suspension is not part of the same pharmacological class as these products. These products are structural fillers that are injected into facial tissue to smooth wrinkles and folds, by temporarily adding volume to facial tissue. The fibroblast dosage formulation operates by a very different proposed mechanism of action. The dosage formulation units described herein are useful for the treatment of rhytids, nasolabial and melolabial folds, perioral lines, lateral canthal lines, periorbital lines, and glabellar lines.

The fibroblast dosage formulation is also useful for providing pluripotent cells for tissue repair and regeneration.

DETAILED DESCRIPTION OF THE INVENTION

Figure 1:
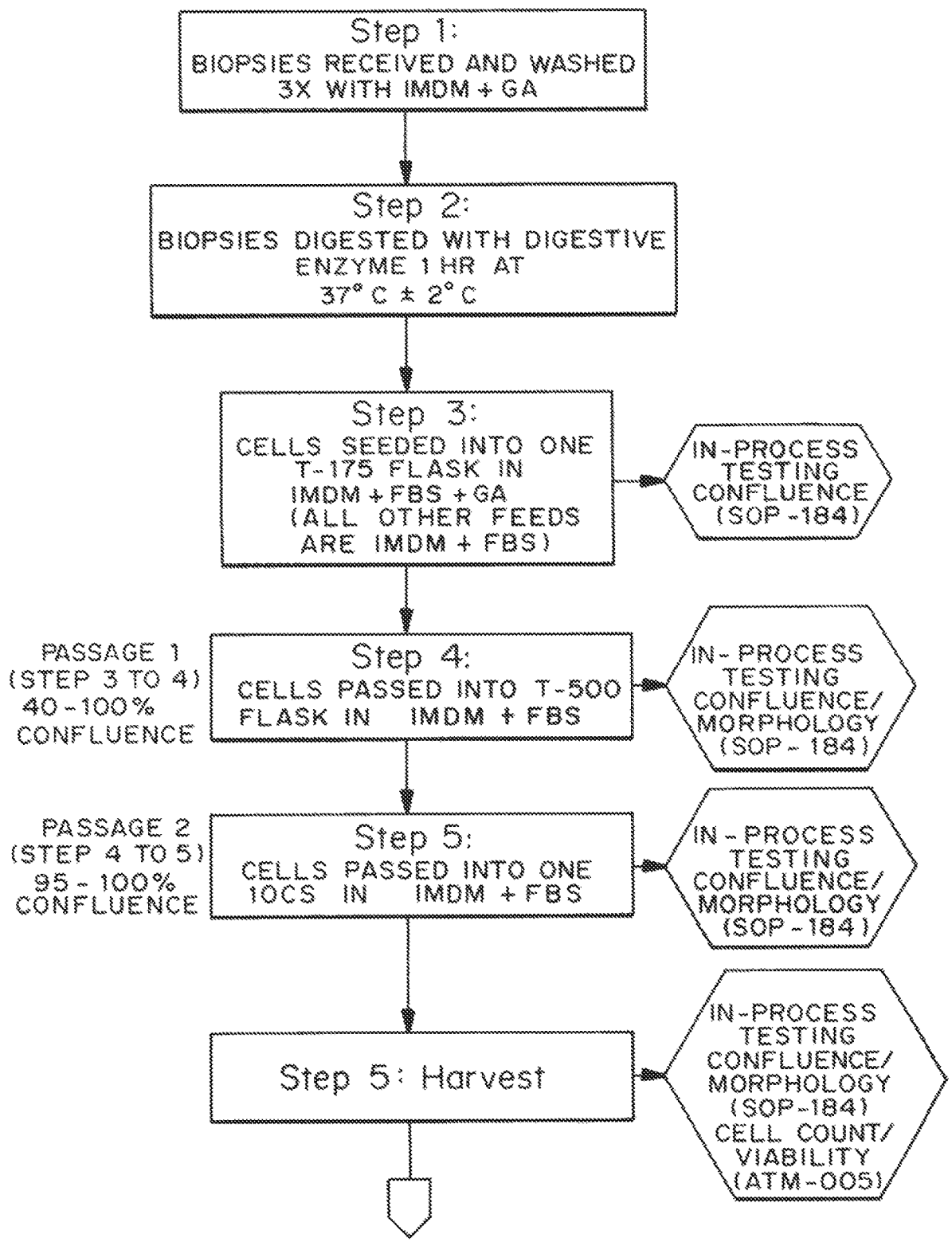
FIG. 1 is a standardized manufacturing process flow diagram.
Figure 1:
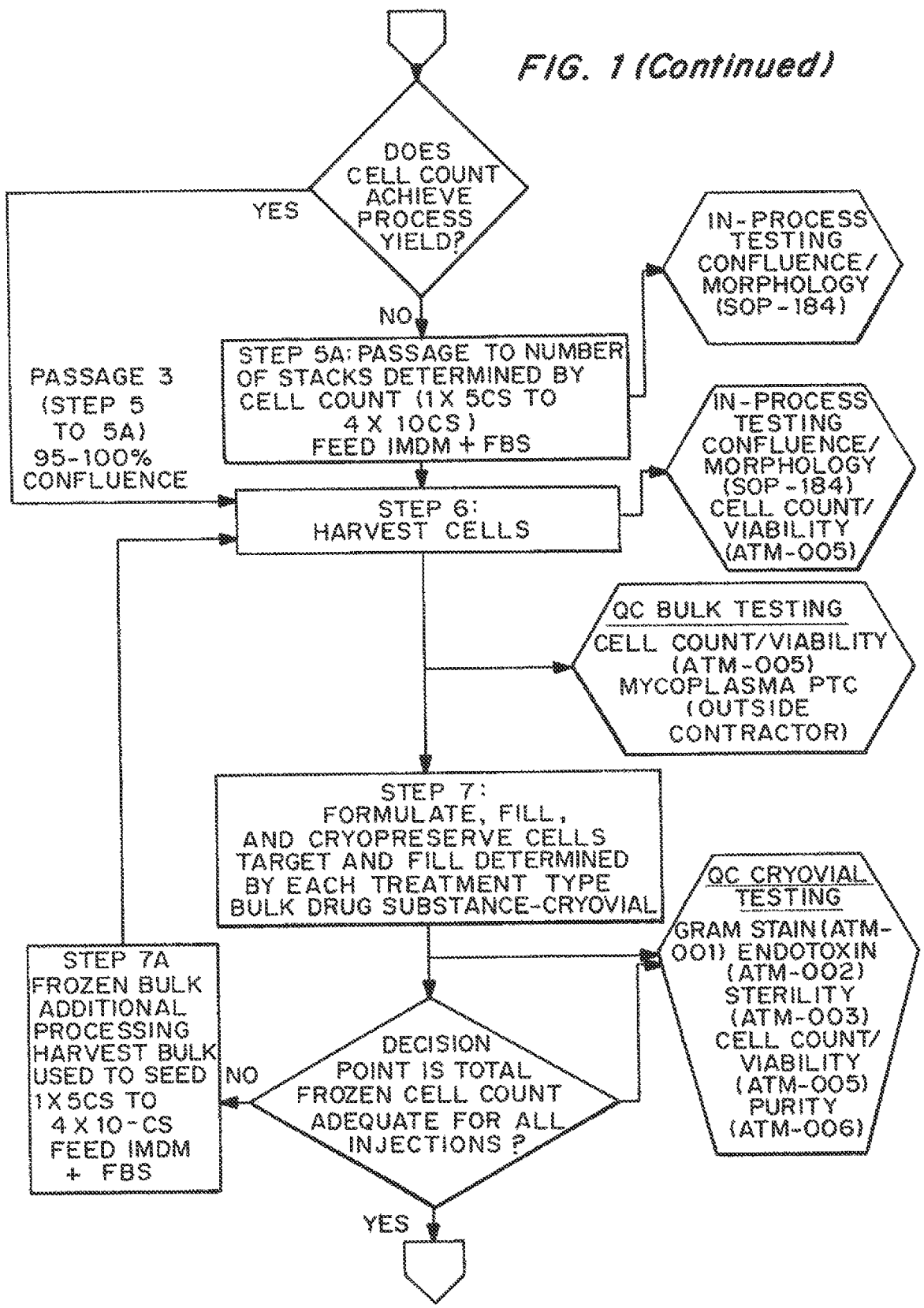
Figure 1:
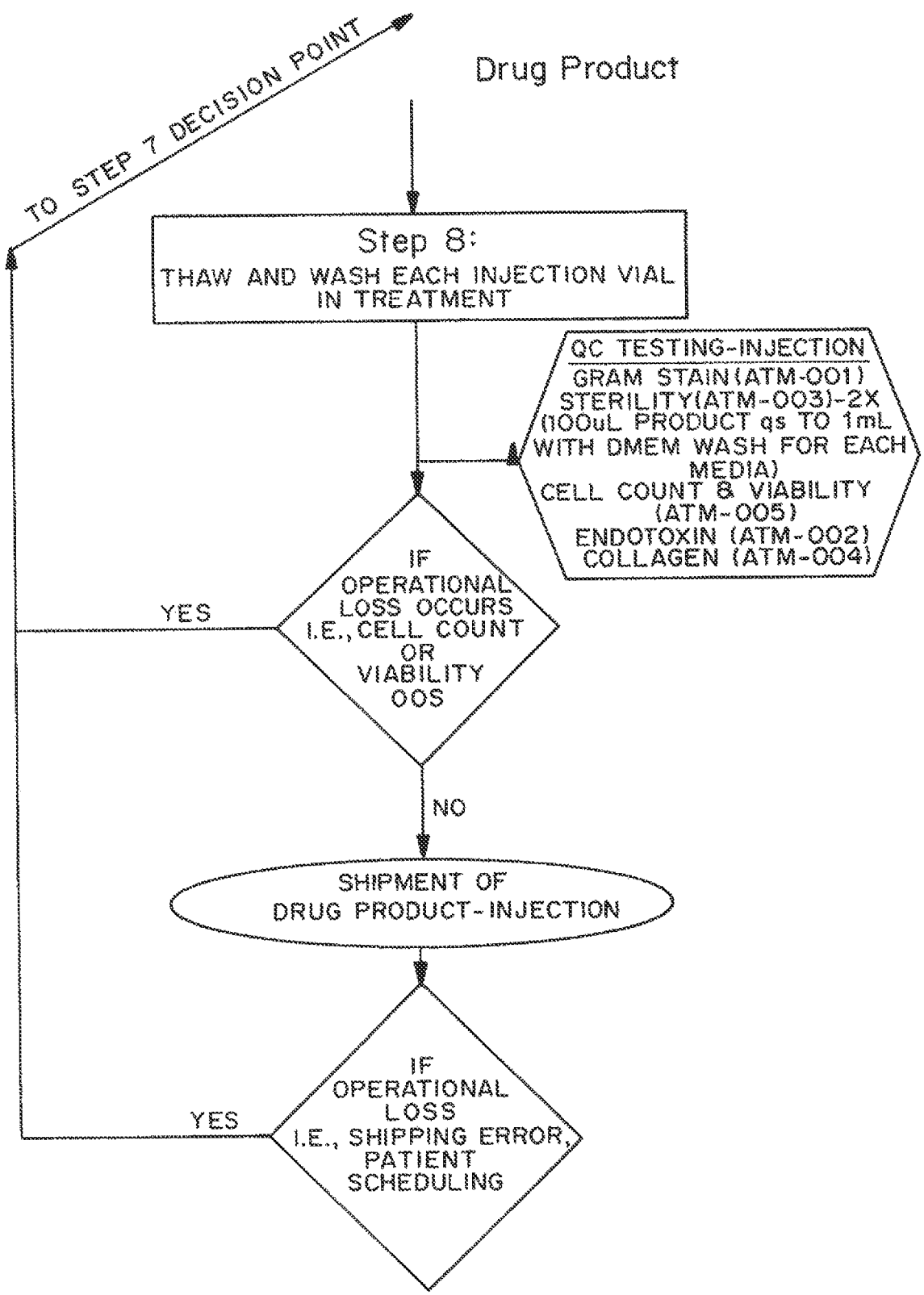

An autologous fibroblast product has been developed. The cell therapy product is composed of a suspension of autologous fibroblasts, grown from a biopsy of each individual's own skin using standard tissue culture procedures. Skin tissue (dermis and epidermis layers) is biopsied from a patient's post-auricular area and shipped via next day delivery to a manufacturing facility at 2-8° C. Fibroblasts isolated from the tissue via enzymatic digestion are expanded to a quantity sufficient for injection into the patient's target treatment area. The Cell therapy product consists of expanded fibroblasts, formulated to the target Cell therapy product cell concentration and cryopreserved in cryovials, called Bulk Drug Substance—Cryovial. The final cell therapy product consists of thawed Bulk Cell therapy product—Cryovial cells that are thawed, washed and prepared for patient injection.

Initial marketing approval is for the treatment of moderate to severe nasolabial fold wrinkles. The current clinical development is focused on the treatment of dermal contour deformities, vocal cord scarring, gingival recessions, restrictive burn scars, and acne scarring. The dosage and administration regime are different, depending on the condition to be treated, as discussed below. Although the exact mechanism is unknown, the autologous fibroblasts that comprise the active component of the fibroblast dosage formulation are thought to increase the synthesis of extracellular matrix components such as collagen when injected into patient skin, thus increasing skin integrity and ultimately leading to a decrease in fine lines and wrinkles.

The following definitions are used herein:
ATM Analytical Test Method
AZFICEL-T USAN nomenclature for autologous cultured fibroblasts
BULK HARVEST material following final harvest prior to formulation in cryopreservation media
CGMP Current Good Manufacturing Practice
CS Cell stack
DMEM Dulbecco's Modification of Eagle's Medium
DMSO Dimethyl sulfoxide
DRUG PRODUCT—INJECTION material washed and reformulated in DMEM, vialed and ready for shipment to clinical sites
DRUG SUBSTANCE—CRYOVIAL material formulated in cryopreservation media and aliquoted into cryovials
EDTA Ethylenediaminetetra acetic acid
FACS Fluorescence Activated Cell Sorting
FBS Fetal Bovine Serum
GA Gentamicin and Amphotericin B
IMDM Iscove's Modified Dulbecco's Medium
IND Investigational New Drug application
PBS Phosphate Buffered Saline
PCA Personal Cell Analysis
QC Quality Control
USP United States Pharmacopeia I. Dosage Unit Formulations A. Sources of Cells 1. Autologous Dermal Fibroblasts The cells in the formulation display typical fibroblast morphologies when growing in cultured monolayers. Specifically, cells may display an elongated, fusiform or spindle appearance with slender extensions, or cells may appear as larger, flattened stellate cells which may have cytoplasmic leading edges. A mixture of these morphologies may also be observed. The cells express proteins characteristic of normal fibroblasts including the fibroblast-specific marker, CD90 (Thy-1), a 35 kDa cell-surface glycoprotein, and the extracellular matrix protein, collagen. The fibroblast dosage formulation is an autologous cell therapy product composed of a suspension of autologous fibroblasts, grown from a biopsy of each individual's own skin using standard tissue culture procedures. Skin tissue (dermis and epidermis layers) is biopsied from a patient's post-auricular area.

2. Precursor Cells

Figure 2:
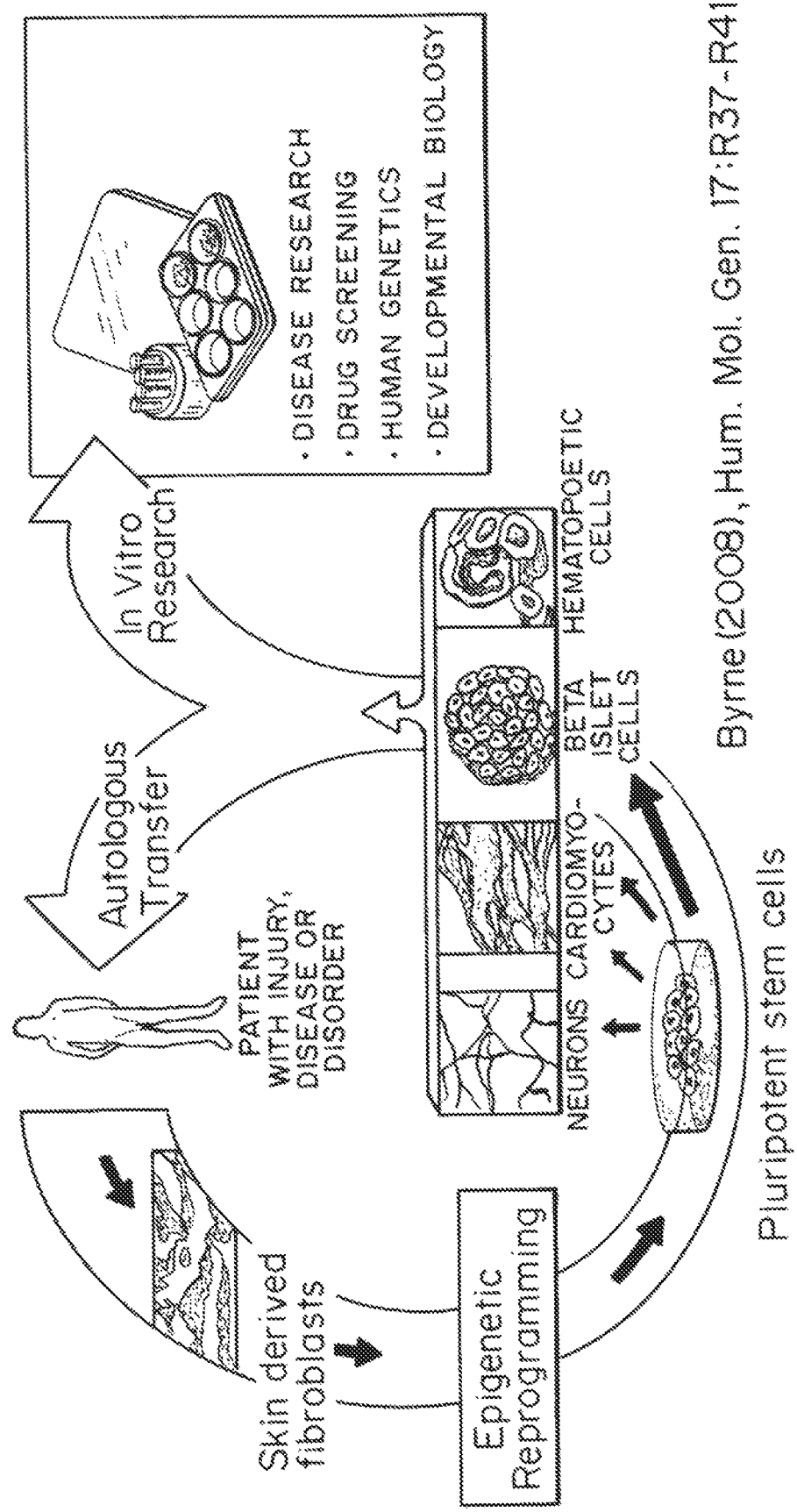
FIG. 2 is a schematic from Byrne 2008 Hum. Mol. Gen. 17:R37-R41, showing how skin derived fibroblasts can be de-differentiated using epigenetic reprogramming into pluripotent stem cells, which can then differentiate into neurons, cardiomyocytes, beta islet cells, and hematopoetic cells.

The fibroblasts can also be used to create other cell types for tissue repair or regeneration. Derivation of embryonic stem (ES) cells genetically identical to a patient by somatic cell nuclear transfer (SCNT) holds the potential to cure or alleviate the symptoms of many degenerative diseases while circumventing concerns regarding rejection by the host immune system. Byrne, et al. Nature 2007 Nov. 22; 450 (7169):497-502, used a modified SCNT approach to produce rhesus macaque blastocysts from adult skin fibroblasts, and successfully isolated two ES cell lines from these embryos. DNA analysis confirmed that nuclear DNA was identical to donor somatic cells and that mitochondrial DNA originated from oocytes. Both cell lines exhibited normal ES cell morphology, expressed key stem-cell markers, were transcriptionally similar to control ES cells and differentiated into multiple cell types in vitro and in vivo. See also Sparman, et al. Stem Cells 2009; 27(6):1255-64. FIG. 2 is a schematic from Byrne 2008 Hum. Mol. Gen. 17:R37-R41, showing how skin derived fibroblasts can be de-differentiated using epigenetic reprogramming into pluripotent stem cells, which can then differentiate into neurons, cardiomyocytes, beta islet cells, and hematopoetic cells. See Hochedlinger, et al., Development. 2009 February; 136(4): 509-23 and Kanawaty, et al. Bioessays. 2009 February; 31(2):134-8.

Figure 3:
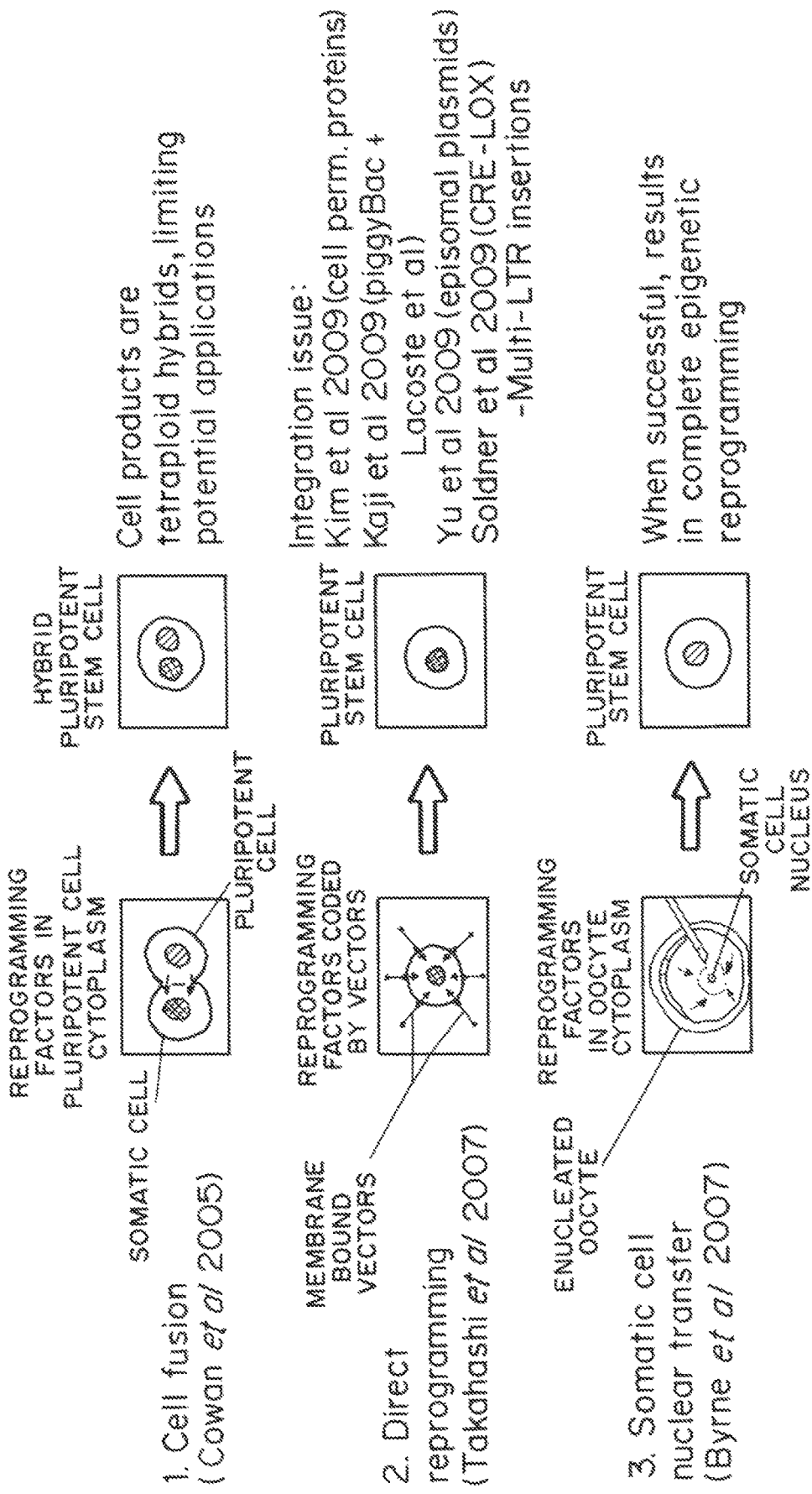
FIG. 3 is a schematic of methods by which fibroblasts can be de-differentiated into pluripotent cells: cell fusion (Cowan et al. 2005), direct reprogramming (Takahashi, et al., 2007), and somatic cell nuclear transfer (Byrne, et al. 2007).

FIG. 3 is a schematic of methods by which fibroblasts can be de-differentiated into pluripotent cells: cell fusion (Cowan et al. Science. 2005 Aug. 26; 309(5739):1369-73), direct reprogramming (Takahashi, et al., Cell. 2007 30; 131(5):861-72), and somatic cell nuclear transfer (Byrne, et al, 2007). Takahashi, et al. demonstrated the generation of iPS cells from adult human dermal fibroblasts with the same four factors: Oct3/4, Sox2, Klf4, and c-Myc. Human iPS cells were similar to human embryonic stem (ES) cells in morphology, proliferation, surface antigens, gene expression, epigenetic status of pluripotent cell-specific genes, and telomerase activity. Furthermore, these cells could differentiate into cell types of the three germ layers in vitro and in teratomas. These findings demonstrate that iPS cells can be generated from adult human fibroblasts.

B. Preparation of Cells

The autologous fibroblasts in the Drug Substance are derived by outgrowth from a biopsy of the recipient's own skin followed by expansion in culture using standard cell culture techniques. Skin tissue (dermis and epidermis layers) is biopsied from a subject's post-auricular area. The starting material is composed of three 3-mm punch skin biopsies collected using standard aseptic practices. The biopsies are collected by the treating physician, placed into a vial containing sterile phosphate buffered saline (PBS). The biopsies are shipped in a 2-8° C. refrigerated shipper back to the manufacturing facility.

After arrival at the manufacturing facility, the biopsy is inspected and, upon acceptance, transferred directly to the manufacturing area. Upon initiation of the process, the biopsy tissue is then washed prior to enzymatic digestion. After washing, a Liberase Digestive Enzyme Solution is added without mincing, and the biopsy tissue is incubated at 37.0±2° C. for one hour. Time of biopsy tissue digestion is a critical process parameter that can affect the viability and growth rate of cells in culture. Liberase is a collagenase/neutral protease enzyme cocktail obtained formulated from Lonza Walkersville, Inc. (Walkersville, Md.) and unformulated from Roche Diagnostics Corp. (Indianapolis, Ind.). Alternatively, other commercially available collagenases may be used, such as Serva Collagenase NB6 (Helidelburg, Germany). After digestion, Initiation Growth Media (IMDM, GA, 10% Fetal Bovine Serum (FBS)) is added to neutralize the enzyme, cells are pelleted by centrifugation and resuspended in 5.0 mL Initiation Growth Media. Alternatively, centrifugation is not performed, with full inactivation of the enzyme occurring by the addition of Initiation Growth Media only. Initiation Growth Media is added prior to seeding of the cell suspension into a T-175 cell culture flask for initiation of cell growth and expansion. A T-75, T-150, T-185 or T-225 flask can be used in place of the T-75 flask.

Cells are incubated at 37±2.0° C. with 5.0±1.0% $CO_2$ and fed with fresh Complete Growth Media every three to five days. All feeds in the process are performed by removing half of the Complete Growth Media and replacing the same volume with fresh media. Alternatively, full feeds can be performed. Cells should not remain in the T-175 flask greater than 30 days prior to passaging. Confluence is monitored throughout the process to ensure adequate seeding densities during culture splitting. When cell confluence is greater than or equal to 40% in the T-175 flask, they are passaged by removing the spent media, washing the cells, and treating with Trypsin-EDTA to release adherent cells in the flask into the solution. Cells are then trypsinized and seeded into a T-500 flask for continued cell expansion. Alternately, one or two T-300 flasks, One Layer Cell Stack (1 CS), One Layer Cell Factory (1 CF) or a Two Layer Cell Stack (2 CS) can be used in place of the T-500 Flask.

Morphology is evaluated at each passage and prior to harvest to monitor the culture purity throughout the culture purity throughout the process. Morphology is evaluated by comparing the observed sample with visual standards for morphology examination of cell cultures. The cells display typical fibroblast morphologies when growing in cultured monolayers. Cells may display either an elongated, fusiform or spindle appearance with slender extensions, or appear as larger, flattened stellate cells which may have cytoplasmic leading edges. A mixture of these morphologies may also be observed. Fibroblasts in less confluent areas can be similarly shaped, but randomly oriented. The presence of keratinocytes in cell cultures is also evaluated. Keratinocytes appear round and irregularly shaped and, at higher confluence, they appear organized in a cobblestone formation. At lower confluence, keratinocytes are observable in small colonies.

Cells are incubated at 37 d 2.0° C. with 5.0±1.0% $CO_2$ and fed every three to five days in the T-500 flask and every five to seven days in the ten layer cell stack (10 CS). Cells should not remain in the T-500 flask for more than 10 days prior to passaging. Quality Control (QC) release testing for safety of the Bulk Drug Substance includes sterility and endotoxin testing. When cell confluence in the T-500 flask is ≥95%, cells are passaged to a 10 CS culture vessel. Alternately, two Five Layer Cell Stacks (5 CS) or a 10 Layer Cell Factory (10 CF) can be used in place of the 10 CS. 10 CS. Passage to the 10 CS is performed by removing the spent media, washing the cells, and treating with Trypsin-EDTA to release adherent cells in the flask into the solution. Cells are then transferred to the 10 CS. Additional Complete Growth Media is added to neutralize the trypsin and the cells from the T-500 flask are pipetted into a 2 L bottle containing fresh Complete Growth Media. The contents of the 2 L bottle are transferred into the 10 CS and seeded across all layers. Cells are then incubated at 37±2.0° C. with 5.0±1.0% $CO_2$ and fed with fresh Complete Growth Media every five to seven days. Cells should not remain in the 10 CS for more than 20 days prior to passaging.

The passaged dermal fibroblasts are rendered substantially free of immunogenic proteins present in the culture medium by incubating the expanded fibroblasts for a period of time in protein free medium, Primary Harvest: When cell confluence in the 10 CS is 95% or more, cells are harvested. Harvesting is performed by removing the spent media, washing the cells, treating with Trypsin-EDTA to release adherent cells into the solution, and adding additional Complete Growth Media to neutralize the trypsin. Cells are collected by centrifugation, resuspended, and in-process QC testing performed to determine total viable cell count and cell viability.

For treatment of nasolabial folds, the total cell count must be $3.4 \times 10^8$ cells and viability 85% or higher. Alternatively, total cell yields for other indications can range from $3.4 \times 10^8$ to $1 \times 10^9$ cells. Cell count and viability at harvest are critical parameters to ensure adequate quantities of viable cells for formulation of the Drug Substance. If total viable cell count is sufficient for the intended treatment, an aliquot of cells and spent media are tested for mycoplasma contamination. Mycoplasma testing is performed. Harvested cells are formulated and cryopreserved.

If additional cells are required after receiving cell count results from the primary 10 CS harvest, an additional passage into multiple cell stacks (up to four 10 CS) is performed (Step 5a in FIG. 1). For additional passaging, cells from the primary harvest are added to a 2 L media bottle containing fresh Complete Growth Media. Resuspended cells are added to multiple cell stacks and incubated at 37±2.0° C. with 5.0±1.0% $CO_2$. The cell stacks are fed and harvested as described above, except cell confluence must be 80% or higher prior to cell harvest. The harvest procedure is the same as described for the primary harvest above. A mycoplasma sample from cells and spent media is collected, and cell count and viability performed as described for the primary harvest above.

The method decreases or eliminates immunogenic proteins be avoiding their introduction from animal-sourced reagents. To reduce process residuals, cells are cryopreserved in protein-free freeze media, then thawed and washed prior to prepping the final injection to further reduce remaining residuals. If additional Drug Substance is needed after the harvest and cryopreservation of cells from additional passaging is complete (Step 5a in FIG. 1), aliquots of frozen Drug Substance—Cryovial are thawed and used to seed 5 CS or 10 CS culture vessels (Step 7a in FIG. 1). Alternatively, a four layer cell factory (4 CF), two 4 CF, or two 5 CS can be used in place of a 5 CS or 10 CS. A frozen cryovial(s) of cells is thawed, washed, added to a 2 L media bottle containing fresh Complete Growth Media and cultured, harvested and cryopreserved as described above. The cell suspension is added Cell confluence must be 80% or more prior to cell harvest.

C. Preparation of Cell Suspension

At the completion of culture expansion, the cells are harvested and washed, then formulated to contain $1.0$-$2.7 \times 10^7$ cells/mL, with a target of $2.2 \times 10^7$ cells/mL. Alternatively, the target can be adjusted within the formulation range to accommodate different indication doses. The drug substance consists of a population of viable, autologous human fibroblast cells suspended in a cryopreservation medium consisting of Iscove's Modified Dulbecco's Medium (IMDM) and Profreeze-CDM™ (Lonza, Walkerville, Md.) plus 7.5% dimethyl sulfoxide (DMSO). Alternatively, a lower DMSO concentration may be used in place of 7.5% or CryoStor™ CS5 or CryoStor™ CS10 (BioLife Solutions, Bothell, Wash.) may be used in place of IMDM/Profreeze/DMSO. The freezing process consists of a control rate freezing step to the following ramp program:
STEP 1: Wait at 4.0 C
STEP 2: 1.0° C./minC/m to −4.0° C. (sample probe)
STEP 3: 25.0° C./minC/m to −40° C. (chamber probe)
STEP 4: 10.0° C./minC/m to −12.0° C. (chamber probe)
STEP 5: 1.0° C./minC/m to −40° C. (chamber probe)
STEP 6: 10.0° C./minC/m to −90° C. (chamber probe)
STEP 7: End After completion of the controlled rate freezing step, Bulk Drug Substance vials are transferred to a cryogenic freezer for storage in the vapor phase. After cryogenic freezing, the Drug Substance is submitted for Quality Control testing. Drug Substance specifications also include cell count and cell viability testing performed prior to cryopreservation and performed again for Drug Substance—Cryovial. Viability of the cells must be 85% or higher for product release. Cell count and viability are conducted using an automated cell counting system (Guava Technologies), which utilizes a combination of permeable and impermeable fluorescent, DNA-intercalating dyes for the detection and differentiation of live and dead cells. Alternatively, a manual cell counting assay employing the trypan blue exclusion method may be used in place of the automated cell method above. Alternatively, other automated cell counting systems may be used to perform the cell count and viability method, including Cedex (Roche Innovatis AG, Bielefeld, Germany), ViaCell™ (Beckman Coulter, Brea, Calif.), NuceloCounter™ (New Brunswick Scientific, Edison, N.J.), Countless® (Invitrogen, division of Life Technologies, Carlsbad, Calif.), or Cellometer® (Nexcelom Biosciences, Lawrence, Mass.). Drug Substance—Cryovial samples must meet a cell count specification of $1.0$-$2.7 \times 10^7$ cells/mL prior to release. Sterility and endotoxin testing are also conducted during release testing.

In addition to cell count and viability, purity/identity of the Drug Substance is performed and must confirm the suspension contains 98% or more fibroblasts. The usual cell contaminants include keratinocytes. The purity/identify assay employs fluorescent-tagged antibodies against CD90 and CD104 (cell surface markers for fibroblast and keratinocyte cells, respectively) to quantify the percent purity of a fibroblast cell population. CD90 (Thy-1) is a 35 kDa cell-surface glycoprotein. Antibodies against CD90 protein have been shown to exhibit high specificity to human fibroblast cells. CD104, integrin β4 chain, is a 205 kDa transmembrane glycoprotein which associates with integrin α6 chain (CD49f) to form the α6/β4 complex. This complex has been shown to act as a molecular marker for keratinocyte cells (Adams and Watt 1991).

Antibodies to CD104 protein bind to 100% of human keratinocyte cells. Cell count and viability is determined by incubating the samples with Viacount Dye Reagent and analyzing samples using the Guava PCA system. The reagent is composed of two dyes, a membrane-permeable dye which stains all nucleated cells, and a membrane-impermeable dye which stains only damaged or dying cells. The use of this dye combination enables the Guava PCA system to estimate the total number of cells present in the sample, and to determine which cells are viable, apoptotic, or dead. The method was custom developed specifically for use in determining purity/identity of autologous cultured fibroblasts. The specific procedure is as follows:

Procedure

Preparation of 25% (W/V) Sodium Azide in PBS

Preparation of FACS (Fluorescent Activated Cell Sorting) Buffer:

In a 1000 mL Nalgene bottle, combine 966 mL of PBS, 30 mL of FBS and 4 mL of 25% sodium azide solution in PBS.

Preparation of 1% (v/v) HuS in PBS:

Prepare 1 mL of 1% HuS in PBS per sample tested. Into a 1.5 mL tube labeled 1% HuS aliquot 990 μL of PBS. Add 10 μL of Human Serum to the tube labeled 1% HuS.

Sample Receipt and Preparation:

Verify that the daily Guava Check has been performed for the day with passing results. Perform cell count and viability assay using the Guava PCA on the testing vials. Record the mean cell count value obtained.

For each sample set, per test vial, label four 1.5 mL microcentrifuge tubes as follows: "CD90," "CD104," "Mouse" (corresponding to mouse IgG1 isotype control), and "Rat" (corresponding to rat IgG2b Isotype control).

Using the mean cell count result, calculate the appropriate volume of cells to aliquot so that each tube receives $1 \times 10^5$ viable cells.

Example:

If the mean viable cell count result documented is $1.5 \times 10^7$ cells/mL, divide $1 \times 10^5$ by $1.5 \times 10^7$ cells/mL for the appropriate volume. Multiply this volume (mL) by 1000 to convert the unit into μL.

$1 \times 10^5 / 1.5 \times 10^7$ cells/mL=0.0066 mL×1000=7 μL of cell solution aliquot.

Add sufficient FACS buffer to each tube so that the total volume will be 1 mL.

Example:

If the cell solution added is 7 μL, then subtract 7 μL from 1 mL, or 1000 μL. 1000 μL-7 μL=993 μL FACS buffer added.

Mix the testing vial by vortexing continuously on vortex setting 8 for 3 seconds.

Add the appropriate amount of cell solution to the FACS buffer. Mix by vortexing continuously on vortex setting 8 for 3 seconds.

Pellet the cells in each sample tube by centrifugation at 3,000 rpm for 3 minutes. If difficulty in pellet formation arises, then centrifuge tubes again at 3,000 rpm for 3 minutes. If pellet formation is adequate after the second centrifugation proceed with aspirating the supernatant. With the aid of a pipette, aspirate the supernatant into a waste container containing 20% bleach in DI water. Leave approximately 50 µL of supernatant in each tube to minimize inadvertently aspirating cells.

Add 200 µL of 1% HuS in PBS. Mix by vortexing continuously on vortex setting 8 for 3 seconds.

Incubate tubes for 25 minutes±5 minutes at 2-8° C.

Add 5.0 µL of antibody or isotype control to the respective tube. Mix by vortexing continuously on vortex setting 8 for 3 seconds.

Incubate tubes for 25 minutes±5 minutes at 2-8° C. Protect from light.

Add 800 µL of FACS buffer to each tube. Mix by vortexing continuously on vortex setting 8 for 3 seconds.

With the aid of a pipette, aspirate the supernatant and leave approximately 50 µL of supernatant in each tube to minimize inadvertently aspirating cells, Add 400 µL of FACS buffer. Mix by vortexing continuously on vortex setting 8 for 3 seconds.

Sample Acquisition Using the Guava PCA:

Open CytoSoft 2.1.5 and click Guava Express from the main menu.

Click New Data Set and follow the screen commands to create a new file. Ensure that 2000 is entered in the Events To Acquire section of the Guava Express Acquisition screen. Adjust the settings for the mouse IgG1 isotype control. Within the sample information control panel enter the sample Part, Lot and isotype control or antibody (e.g., "DR01 200502001_mouse") to identify each sample in the Sample ID field.

Vortex the mouse IgG1 isotype control tube continuously on vortex setting 8 for 3 seconds, load it into the Guava PCA and click Settings. A message window will appear, choose Adjust Settings. Another message window will appear prompting to load the control sample, choose OK.

The "Adjust Settings" screen should appear and the system will automatically set the threshold to exclude background fluorescence. Select an FSC Gain intensity to position the center of the defined cell cluster over 10e3 in the lower right quadrant on the X-axis of the FSC vs. Viability (PM1) plot (e.g., "x2"). Position the FSC threshold bar on the FSC vs. Viability (PM1) plot to exclude debris.

Adjust the PM2 to 300 V. Adjust the PM1 between 300-400 V, so that the negative control population is positioned between 10e0 and 10e1 on both FSC vs PM1 and PM1 vs PM2 dot plots.

Acquire Mouse IgG1 Isotype Control:

Vortex the mouse IgG1 isotype control tube continuously on vortex setting 8 for 3 seconds, load it into the Guava PCA and click Acquire Next Sample. Ensure that all of the default gating options are set to ungated. On the PM1 Fluorescence vs Count histogram the markers are set in a default position. Click on the marker to set it so that the % of Histogram Events for the PM1 Gated sample is at approximately 1.0%.

Acquire CD90 Sample:

Within the sample information control panel enter the sample Part, Lot and isotype control or antibody (e.g., "DR01 200502001_CD90") to identify each sample in the Sample ID field. Verify that the PM1 fluorescence markers are set to the same settings as the mouse IgG1 isotype control sample.

Adjust Settings for the Rat IgG2b Isotype Control:

Vortex the rat IgG1 isotype control tube continuously on vortex setting 8 for 3 seconds, load it into the Guava PCA and click Settings. The "Adjust Settings" screen should appear and the system will automatically set the threshold to exclude background fluorescence. Select an FSC Gain intensity to position the center of the defined cell cluster over $10^3$ in the lower right quadrant on the X-axis of the FSC vs. Viability (PM1) plot (e.g., "x2"). Position the FSC threshold bar on the FSC vs. Viability (PM1) plot to exclude debris. Adjust the PM2 to 300 V. Adjust the PM1 between 300-400 V, so that the negative control population is positioned between 10e0 and 10e1 on both FSC vs PM1 and PM1 vs. PM2 dot plots.

Acquire Rat IgG1 Isotype Control Sample:

Vortex the rat IgG1 isotype control tube continuously on vortex setting 8 for 3 seconds, load it into the Guava PCA and click Acquire Next Sample. Set all of the gating options to ungated. On the PM1 Fluorescence vs Count histogram the markers are set in a default position. Click on the marker to set it so that the % of Histogram Events for the PM1 Gated sample is at approximately 1.0%. The position of the marker is displayed as a numeric value in the "Marker Position" box.

Acquire CD104 Sample:

Vortex the CD104 tube continuously on vortex setting 8 for 3 seconds, load it into the Guava PCA and click Acquire Next Sample. Verify that the PM1 fluorescence markers are set to the same settings as the rat IgG1 isotype control sample.

Sample Analysis Using the Guava PCA:

Click Go to Analysis from the Acquisition screen. Click Print and then OK. Initial and date each of the printed reports.

Purity Calculations:

PM1 Events Count [total events labeled with CD90 (CD90)]−PM1 Events Count [total events labeled with anti-CD90 (Mouse IgG1)]=Total events (normalized for background/non-specific fluorescence) labeled with CD90 (e.g., 1918 events−20 events=1898 events).

PM1 Events Count [total events labeled with CD104 (CD104)]−PM1 Events Count [total events labeled with anti-CD104 (Rat IgG2b)]=Total events (normalized for background/non-specific fluorescence) labeled with CD104 (e.g., 31 events−23 events=8 events).

Total events (normalized for background/non-specific fluorescence) labeled with CD90+Total events (normalized for background/non-specific fluorescence) labeled with CD104=Total normalized labeled events (e.g., 1898 events+8 events=1906 events)

Calculate the % purity as follows: 1898 Total CD90 events/1906 Total normalized labeled events×100=99.58, or 100%.

System Suitability and Specification:

Successful Bead Check must be performed prior to the start of the assay. Total Particles Count must acquire 2000. Purity percentage for all samples must be ≥98%.

Alternate Manufacturing Methods

Alternatively, cells can be passaged from either the T-175 flask (or alternatives) or the T-500 flask (or alternatives) into a spinner flask containing microcarriers as the cell growth surface. Microcarriers are small bead-like structures that are used as a growth surface for anchorage dependent cells in suspension culture. They are designed to produce large cell yields in small volumes.

In this apparatus, a volume of Complete Growth Media ranging from 50 mL-300 mL is added to a 500 mL, IL or 2 L sterile disposable spinner flask. Sterile microcarriers are added to the spinner flask. The culture is allowed to remain static or is placed on a stir plate at a low RPM (15-30 RRM)

for a short period of time (1-24 hours) in a 37±2.0° C. with 5.0±1.0% $CO_2$ incubator to allow for adherence of cells to the carriers. After the attachment period, the speed of the spin plate is increased (30-120 RPM). Cells are fed with fresh Complete Growth Media every one to five days, or when media appears spent by color change.

Cells are collected at regular intervals by sampling the microcarriers, isolating the cells and performing cell count and viability analysis. The concentration of cells per carrier is used to determine when to scale-up the culture. When enough cells are produced, cells are washed with PBS and harvested from the microcarriers using trypsin-EDTA and seeded back into the spinner flask in a larger amount of microcarriers and higher volume of Complete Growth Media (300 mL-2 L). Alternatively, additional microcarriers and Complete Growth Media can be added directly to the spinner flask containing the existing microcarrier culture, allowing for direct bead-to-bead transfer of cells without the use of trypsinizationtrypsiziation and reseeding. Alternatively, if enough cells are produced from the initial T-175 or T-500 flask, the cells can be directly seeded into the scale-up amount of microcarriers.

After the attachment period, the speed of the spin plate is increased (30-120 RPM). Cells are fed with fresh Complete Growth Media every one to five days, or when media appears spent by color change. When the concentration reaches the desired cell count for the intended indication, the cells are washed with PBS and harvested using trypsin-EDTA. All release testing, cryopreservation and preparation of Drug Product—Injection would follow the process described in Sections C and D.

Microcarriers used within the disposable spinner flask may be made from poly blend such as BioNOC II® (Cesco Bioengineering, distributed by Bellco Biotechnology, Vineland, N.J.) and FibraCel® (New Brunswick Scientific, Edison, N.J.), gelatin, such as Cultispher-G (Percell Biolytica, Astrop, Sweden), cellulose, such as Cytopore™ (GE Healthcare, Piscataway, N.J.) or coated/uncoated polystyrene, such as 2D MicroHex™ (Nunc, Weisbaden, Germany), Cytodex® (GE Healthcare, Piscataway, N.J.) or Hy-Q Sphere™ (Thermo Scientific Hyclone, Logan, Utah).

Alternatively, cells can be processed on poly blend 2D microcarriers such as BioNOC II® and FibraCel® using an automatic bellow system, such as FibraStage™ (New Brunswick Scientific, Edison, N.J.) or BelloCell® (Cesco Bioengineering, distributed by Bellco Biotechnology, Vineland, N.J.) in place of the spinner flask apparatus. Cells from the T-175 (or alternatives) or T-500 flask (or alternatives) are passaged into a bellow bottle containing microcarriers with the appropriate amount of Complete Growth Media, and placed into the system. The system pumps media over the microcarriers to feed cells, and draws away media to allow for oxygenation in a repeating fixed cycle. Cells are monitored, fed, washed and harvested in the same sequence as described above. Alternatively, cells can be processed using automated systems. After digestion of the biopsy tissue or after the first passage is complete (T-175 flask or alternative), cells may be seeded into an automated device. One method is an Automated Cellular Expansion (ACE) system, which is a series of commercially available or custom fabricated components linked together to form a cell growth platform in which cells can be expanded without human intervention. Cells are expanded in a cell tower, consisting of a stack of disks capable of supporting anchorage-dependent cell attachment. The system automatically circulates media and performs trypsinizationtrypsiziation for harvest upon completion of the cell expansion stage.

Alternatively, the ACE system can be a scaled down, single lot unit version comprised of a disposable component that consists of cell growth surface, delivery tubing, media and reagents, and a permanent base that houses mechanics and computer processing capabilities for heating/cooling, media transfer and execution of the automated programming cycle. Upon receipt, each sterile irradiated ACE disposable unit will be unwrapped from its packaging and loaded with media and reagents by hanging pre-filled bags and connecting the bags to the existing tubing via aseptic connectors. The process continues as follows:

Inside a biological safety cabinet (BSC), a suspension of cells from a biopsy that has been enzymatically digested is introduced into the "pre-growth chamber" (small unit on top of the cell tower), which is already filled with Initiation Growth Media containing antibiotics. From the BSC, the disposable would be transferred to the permanent ACE unit already in place.

After approximately three days, the cells within the pre-growth chamber are trypsinized and introduced into the cell tower itself, which is pre-filled with Complete Growth Media. Here, the "bubbling action" caused by $CO_2$ injection force the media to circulate at such a rate that the cells spiral downward and settle on the surface of the discs in an evenly distributed manner.

For approximately seven days, the cells are allowed to multiply. At this time, confluence will be checked (method unknown at time of writing) to verify that culture is growing. Also at this time, the Complete Growth Media will be replaced with fresh Complete Growth Media. CGM will be replaced every seven days for three to four weeks. At the end of the culture period, the confluence is checked once more to verify that there is sufficient growth to possibly yield the desired quantity of cells for the intended treatment.

If the culture is sufficiently confluent, it is harvested. The spent media (supernatant) is drained from the vessel. PBS will then is pumped into the vessel (to wash the media, FBS from the cells) and drained almost immediately. Trypsin-EDTA is pumped into the vessel to detach the cells from the growth surface. The trypsin/cell mixture is drained from the vessel and enter the spin separato. Cryopreservative is pumped into the vessel to rinse any residual cells from the surface of the discs, and be sent to the spin separator as well. The spin separator collects the cells and then evenly resuspend the cells in the shipping/injection medium. From the spin separator, the cells will be sent through an inline automated cell counting device or a sample collected for cell count and viability testing via laboratory analyses. Once a specific number of cells has been counted and the proper cell concentration has been reached, the harvested cells are delivered to a collection vial that can be removed to aliquot the samples for cryogenic freezing.

Alternatively, automated robotic systems may be used to perform cell feeding, passaging, and harvesting for the entire length or a portion of the process. Cells can be introduced into the robotic device directly after digest and seed into the T-175 flask (or alternative). The device may have the capacity to incubate cells, perform cell count and viability analysis and perform feeds and transfers to larger culture vessels. The system may also have a computerized cataloging function to track individual lots. Existing technologies or customized systems may be used for the robotic option.

D. Dosage Units

Drug Substance—Cryovial used to prepare the final dosage unit consists of fibroblasts that are harvested from the final culture vessel, formulated to the desired cell concentration and cryopreserved in cryovials. Drug Substance- Cryovial is stored in a cryopreservation medium consisting of IMDM and Profreeze™ plus 7.5% DMSO to a target of $2.2\times10^7$ cells/mL. After exposure to a controlled rate freezing cycle, the cryovialed Drug Substance is stored frozen in the vapor phase of a liquid nitrogen freezer.

Harvested cells are pooled, formulated in a cryopreservation media that includes Profreeze, DMSO and IMDM media, aliquoted into cryovials and stored frozen in liquid nitrogen as the Drug Substance—Cryovial material via controlled rate freezing.

The caps and vials are radiation sterilized and received sterile from the manufacturer. The required volume of bulk material needed for treatment is removed from frozen storage, thawed, and pooled. The cells are washed with 4× bulk volume of PBS and centrifuged at 150×g for 10 minutes (5±3° C.). This is followed by a wash with 4× bulk volume of DMEM by resuspension and centrifugation at 150×g for 10 minutes (5±3° C.). The washed cells are resuspended in DMEM without phenol red to a target concentration of $1.0-2.0\times10^7$ cells/mL. Alternatively, the second 4× wash and final resuspension can be performed with Hypothermosol®-FRS (BioLife Solutions, Bothell, Wash.). The final sterile cryovial containers are then manually filled in a Biological Safety Cabinet to a volume of 1.2 mL/container. The Drug Product—Injection is stored at 2-8° C. until shipment in a a 2-8° C. refrigerated shipper to the administration site.

Alternatively, Drug Substance vials can be removed from cryogenic storage and shipped directly to the administration site for dilution and administration. In the direct injection concept, the cells are harvested and prepared for cryopreservation at a higher cell concentration ($3.0-4.0\times10^7$ cell/mL as compared to the current target of $2.2\times10^7$ cells/mL). When an injection is pending, the frozen vial will be shipped to the study site on dry ice or in a liquid nitrogen dewar. The administration site thaws the vial by hand or with a heat block, and performs a 1:1 ratio dilution of the frozen cells at the study site using a typical injection diluent such as bacteriostatic water, sterile water, sodium chloride, or phosphate buffered saline. Alternatively, DMEM may be used as the diluent. This concept eliminates the need to wash and prepare a fresh suspension of the injection for overnight shipment to the study site.

Alternatively, cells freshly harvested from flasks or cells stacks can be adjusted to a target concentration of $1.0-2.0\times10^7$ cells/mL in DMEM, undergo all Bulk Harvest and Drug Substance—Cryovial testing described above and shipped fresh overnight to the administration site in a 2-8° C. refrigerated shipper as the final injection product. In this scenario, sterility and mycoplasma testing may be performed upstream from the harvest to allow time for results prior to shipment.

II. Methods of Administration

A. Preparation of Dosage Units

The azficel-T Azficel-T Drug Product—Injection consists of a suspension of each patient's own living autologous fibroblasts formulated in Dulbecco's Modified Eagle's Medium (DMEM) without phenol red. Azficel-T fibroblast dosage formulation is supplied as two 2 mL vials with each vial containing 1.2 mL of Drug Product at $1.0-2.0\times10^7$ cells/mL. The sterile cellular suspension is intended for intradermal injection. Initially, the cell dosage for Azficel-fibroblast dosage formulation was based on the number of cells administered by clinicians before the regulation of Azficel-T fibroblast dosage formulation by the FDA. A dose range from $1.5-7.0\times10^7$ cells per 1.2-1.4 mL injection was used successfully. Viscosity became a concern for the fibroblast dosage formulation injections in higher concentrations than this range. This dose range converts to $1.1-5.8\times10^7$ cells/mL.

In the first clinical study under IND, $0.5-3.0\times10^7$ cells/mL were formulated. In the second clinical study, $1.0-3.0\times10^7$ cells/mL was formulated. The standard release specification for all subsequent clinical studies was $1.0-2.0\times10^7$ cells/mL.

In the later clinical studies IT-R-005 and IT-R-006, a solution of 1.2 mLs of fibroblasts in each of two 2.0 mL cryovials, formulated to $1.0-2.0\times10^7$ cells/mL, was provided. Of the 2.4 mLs provided, 2.0 mLs were intended for injection at a dosage of 0.1 mL/linear cm, for a maximum predicted nasolabial fold length of 20 total cm on both sides of the face. The 0.2 mL overage is intended to insure 1.0 mL can be obtained from the vial in order to treat up to 10 linear centimeters of naslabial fold.

B. Administration of Dosage Units

Vials are to be warmed to room temperature and gently inverted to resuspend the settled cells. The cellular suspension is withdrawn from the container using a small unit syringe fitted with a detachable needle or with a fixed needle. Use of short, sharp needles and small unit syringes (e.g., 0.5 mL insulin syringes) is recommended for better injection control and to reduce the risk of inflammation. A 29-gauge or 30-gauge needle is required for intradermal injection of the product. However, a syringe with a larger bore 21-gauge detachable needle may be used to aid in withdrawing the product from the container. Once withdrawn, the 21-gauge needle can be switched out with a 30-gauge needle and the product administered.

A batch consists of three injection treatments. For the treatment of nasolabial fold wrinkles, a single injection treatment (batch) requires two 2 mL vials containing 1.2 mL/vial of azficelAzficel-T fibroblast dosage formulation.

C. Conditions to be Treated

The aging process of the skin occurs as a result of both intrinsic and extrinsic factors. The factors that contribute to intrinsic or natural aging are both structural and functional. Structurally, the epidermis becomes thinner, the corneocytes are less adherent and the dermal-epidermal junction is flattened. Functionally, there is a reduction in the number and biosynthetic capacity of fibroblasts and the dermis becomes atrophic and relatively acellular and avascular. Exposure to ultraviolet light radiation is the primary cause of extrinsic or photoaging. Extrinsic aging characteristics are loss of elasticity, increased roughness and dryness, irregular pigmentation, deep wrinkling, a leathery appearance, blister formation and impaired wound healing. The visible appearance of aging, especially facial wrinkles and folds, are common effects that patients seek to reduce. Options for the treatment of facial lines, wrinkles and folds include surgery, neurotoxins, fillers, lasers, non-ablative therapies, microdermabrasion and chemical peels. Many of these treatments vary in safety, efficacy, and duration of effect in the treatment of the signs of aging. The formulation described herein is believed to increase the number of collagen producing cells in the dermis, which may have multifactorial effects for improvement of the skin.

The use of autologous human fibroblasts for treatment of contour deformities was pioneered by William K. Boss, MD, Vice Chairman of the Department of Plastic Surgery at Hackensack University Medical Center. H is work in the area of dermal repair began in 1992. He removed a small piece of skin from a patient's wrist, cultured the autologous fibroblasts from the biopsy, injected the autologous cells into a crease in the skin of the patient's wrist and observed disappearance of the crease over time. He observed the area serially for several years and noted that the test site crease remained corrected. There were no adverse reactions to this single treatment.

A small clinical trial was conducted in March of 1995. Initially, approximately 12 subjects were injected two to three times with autologous cultured fibroblasts in selected rhytids and scars. After 12 months of follow-up, progressive improvement was noted in each subject. Dr. Boss and Dr. Marko reported treating over 100 patients with no signs of allergic or adverse reactions observed over a 2½-year observation period. In December 1995, autologous fibroblasts were made commercially available in the US. US commercial experience included approximately 100 clinicians in the fields of dermatology, facial plastic surgery, and reconstructive plastic surgery, who treated patients with facial rhytids, scars, hypoplastic lips, burns and other problems. There was a reported patient experience of almost 1,000 patients, 354 of whom were included in the efficacy population of an informational retrospective report.

A pilot study using intradermal injections of the fibroblast cell suspension for the treatment of prominent facial rhytids and depressed facial scars was conducted in 10 healthy adults at the University of California Los Angeles (UCLA). Following two (2) injection sessions performed at 3-week intervals, nine out of ten patients noted a 60-100% improvement with the treatment; similar observations were made by the clinicians. A reduction of 10-85% in size of all treated deformities was demonstrated by optical measurements (laser). Microscopically, there was evidence of increased thickness and density of dermal layer.

Studies have shown that the injection of the fibroblast cell suspension into contour deficiencies of the dermis can result in correction of damaged dermal and subcutaneous tissues. Dermis of skin contains fibroblasts which are primarily responsible for the secretion of extracellular matrix components such as collagen and elastin, which provide mechanical strength and integrity to skin. Although the exact mechanism is unknown, the fibroblast cell suspension contains autologous fibroblasts that may increase the synthesis of extracellular matrix components when injected into patient skin, thus increasing skin integrity, ultimately leading to a decrease in fine lines and wrinkles. The effect of the therapy is not immediate, but instead provides a gradual improvement in the appearance of lines and wrinkles over time.

The fibroblast cell suspension was initially evaluated in a clinical study conducted by Dr. William Boss in 1995, and was then marketed in the US as a cosmetic treatment for facial contour deformities from December 1995 to February 1999. After February 1999, FDA was required to regulate for all somatic cell therapies under the PHS Act.

Upon FDA notification that the fibroblast cell suspension would fall under the new cell and tissue regulations, commercial distribution was halted and clinical development under Investigational New Drug Application (IND) #8641 initiated. Studies for the treatment of facial wrinkles and creases in two Phase II studies (Studies IT-R-001 and IT-R-007) and five Phase III studies (Studies IT-R-002, IT-R-003A, IT-R-003B, IT-R-005, and IT-R-006) were conducted. Studies IT-R-003A, IT-R-003B, IT-R-005 and IT-R-006 provide robust, well-controlled data demonstrating the safety and efficacy profile of a fibroblast cell suspension. The fibroblast cell suspension was studied in the treatment of acne scars (Study IT-A-008; IND #13455). Ninety-nine subjects received treatment with the fibroblast cell suspension during Study IT-A-008. The fibroblast cell suspension was also developed for use in other indications including treatment of restrictive burns scars (IND #13308), vocal cord scarring (IND #9892) and gingival repair (IND #10805).

The earlier 001 and 002 trials provided supportive, exploratory data that guided the design of the 003A/B and 005/006 trials Study IT-R-001 was a Phase II double-blind, randomized, and placebo-controlled study of the fibroblast cell suspension for the treatment of rhytids (nasolabial and melolabial folds, perioral lines, glabellar lines, acne scars, and forehead were treated). In the acute phase of the study, each subject received three treatments of the fibroblast cell suspension ($0.5 \times 10^7$, $1.0 \times 10^7$, or $2.0 \times 10^7$ cells/mL) or placebo, administered approximately two weeks apart. Subjects (40) were treated with the fibroblast cell suspension (N=30) or placebo (N=10) in the acute phase of the study.

Study IT-R-002 was a Phase III double-blind, randomized and placebo-controlled study of the fibroblast cell suspension for the treatment of facial contour deformities and scars. In the acute phase of this study, each subject received three treatments of the fibroblast cell suspension containing $2.0 \times 10^7$ cells/mL or placebo, administered every 14±7 days. Subjects (151) were treated with the fibroblast cell suspension (N=112) or placebo (N=39) in the acute phase of the study. Across both studies, subjects (213) were treated with the fibroblast cell suspension (N=100) or placebo (N=113) in the acute phase of the trial.

Although Study IT-R-003B showed efficacy for both of the co-primary endpoints, the failure of one of the co-primary endpoints in Study IT-R-003A to meet the criterion for statistical significance (for the Investigator Evaluation) led to two new protocols as the pivotal Phase III trials for the fibroblast cell suspension (Studies IT-R-005 and IT-R-006). The reasons for the missed endpoint in 003A are believed to have included sub-optimal dosing. The concentration of cells remained the same, but the volume delivered was increased. Other reasons were identified, including training technique and time between injections in the series.

Studies IT-R-005 and IT-R-006 were Phase III multicenter, double-blind, randomized, placebo-controlled studies of the efficacy and safety of the fibroblast cell suspension in the treatment of nasolabial fold wrinkles. These studies were conducted under identical protocols that were subject to an FDA SPA Agreement. In the acute phase of these studies, each subject received three treatments of the fibroblast cell suspension containing $1.0-2.0 \times 10^7$ cells/mL or placebo, administered every five weeks±one week. In Study IT-R-005, 83 subjects were treated with the fibroblast cell suspension and 92 with placebo. In Study IT-R-006, 98 subjects were treated with the fibroblast cell suspension and 99 with placebo.

Study IT-R-007 was a Phase II multicenter, open-label study of the safety and efficacy of the fibroblast cell suspension in the treatment of facial wrinkles and creases, designed to obtain safety and efficacy data for the use of the fibroblast cell suspension for uses other than nasolabial folds. In the acute phase of this study, each subject received two treatments of up to 6 mL of the fibroblast cell suspension containing $1.0-2.0 \times 10^7$ cells/mL, administered every five weeks±10 days. During the acute phase of the study, 45 subjects were treated with the fibroblast cell suspension. This study exposed subjects to a three-fold higher total dose of the fibroblast cell suspension than was used in the 005/006 studies.

The subject populations enrolled into the Phase III pivotal efficacy trials of the fibroblast cells, Studies IT-R-005 and IT-R-006 (005/006), were predominantly White females between 50 and 60 years of age. Subjects ranged in age from 23-82 years, with a mean age of 56.1 years. The severity of subjects' nasolabial fold wrinkles upon enrollment into the study ranged from Grade 3-5 on the Evaluator Wrinkle Severity Assessment scale, with a mean score 37 for the right wrinkle and 3.6 for the left wrinkle.

The populations enrolled into the Phase III IT-R-003A and IT-R-003B (003A/B) studies were similar to those from 005/006. Females comprised 94% of the population in the 003A/B studies, and 95% of the population was White. The mean age of subjects across the two studies was 54.1 years. Although the 003A/B protocol was very similar in design to the 005/006 protocol, 003A/003B permitted the enrollment of subjects with a broader range of wrinkle severity, with scores for the primary nasolabial fold deformity upon enrollment ranging from Grade 2-5 on the Evaluator Scale, but the mean severity score was similar at 3.9.

All pivotal efficacy studies used co-primary endpoints consisting of a subject self-evaluation instrument and an assessment by a clinical investigator. In the 005/006 studies, the co-primary efficacy endpoints were:

Subject Wrinkle Assessment: the subject live comprehensive assessment of the wrinkles of the lower part of the face at visit 6, using a 5-point wrinkle assessment scale, where a response is defined as a two point or better improvement on the scale when compared to baseline.

Evaluator Wrinkle Severity Assessment: the blinded evaluator live assessment of the bilateral nasolabial fold wrinkles at rest, at visit 6, using a 6-point ordinal wrinkle severity scale with a photoguide, where a response is defined as a two point or better improvement on the scale compared to baseline. These endpoints were selected to provide both an impartial assessment (grading by a blinded physician) and clinical relevance (subject's opinion of their own appearance). The scale used for the Evaluator Wrinkle Severity Assessment was the 6-point ordinal wrinkle severity scale for the assessment of nasolabial folds (NLF) developed and validated by Lemperle et al., Plast Reconstr Surg. 2001 108(6):1735-50). The Lemperle scale has been validated to detect a one point improvement in the severity of the nasolabial fold wrinkle. However, because the assessment of appearance can be subjective and prone to variability, success for this endpoint was defined as a two point improvement for each NLF, i.e. for a given patient, both the left and right NLF had to improve by two points in the Evaluator's assessment in order to be considered a responder. The Lemperle scale is an accepted standard of measurement in the field of dermatology, and has been employed successfully in pivotal clinical trials for FDA-approved products in similar indications.

The scale used for the Subject Wrinkle Assessment is based on the published scale used by Cohen and Holmes, Plast Reconstr Surg. 2004 15; 114(4):964-76. As with the Evaluator Assessment, a two-point improvement was established as the criteria for a successful response to treatment.

The 003A/B studies were designed with similar co-primary endpoints, but used a different subject assessment tool than the 005/006 studies. As stated in the 003A/B protocol. The co-primary efficacy endpoints is the efficacy of the fibroblast dosage formulation injection in the primary nasolabial fold at the 6 month visit using the Investigator's 6-point ordinal scale and the Subject's VAS assessment.

The 6-point ordinal scale referenced in the protocol is the same Lemperle scale used in the 005/006 studies, although the 005/006 study provided more descriptive text for each point on the scale than was used in the 003A/B studies. A Visual Analog Scale was used For the Subject assessment. This scale asked subjects to rate each contour deformity from 0 (no defect) to 100 (very severe defect) by placing a mark on a 10 cm line. While both studies met statistical significance for improvement using this assessment tool, the VAS scale was replaced with the ordinal Subject Wrinkle Assessment scale in the 005/006 studies in order to improve the clinical relevance and interpretability of the subject assessment data.

The results of both of the 005/006 studies demonstrated a highly significant difference in response between IT-treated and placebo treated subjects, as measured by both co-primary endpoints.

In the 003A/B studies, statistically significant differences in response between IT-treated and placebo treated subject were observed for three of the four endpoints. In study IT-R-003A, a greater percentage of IT-treated subjects were scored as responders by the Evaluator assessment than placebo-treated subjects, but the difference did not meet statistical significance.

Studies IT-R-005 and IT-R-006 were run concurrently using the same study protocol, so there were no differences in study design. Studies IT-R-003A and IT-R-003B were also run concurrently under separate protocols. Nevertheless, there were differences in results within each study group. All primary endpoints were successfully met in the 005/006 studies, but where the 005 study reported responder rates in the fibroblast cell suspension-treatment group of 57% and 33% for the subject and Evaluator assessments, respectively, the 006 study reported responder rates of 46% and 19% for the same measures. In the 003A study, 21% of subjects in the IT-treatment group were scored as responders in the Evaluator assessment, while 48% of subjects in the fibroblast dosage formulation group responded in Study IT-R-003B according to this measure.

In the 005/006 studies, no significant differences were noted in patient demographics (gender, race, age or baseline severity) between the two trials. However, variability in response rates was observed across sites within each study. Subsequently, all investigators who attended were trained to perform nasolabial fold injection using the same technique, and were expected to prove that they could raise a "wheal" as expected for injection into the papillary dermis. This was not done prior to the IT-R-003 trials. Differences in assessment methods were also observed. The site differences, when coupled with these observations, led to a conclusion that many inconsistencies between sites might be caused by a lack of common training in both injection technique and assessment.

The 005/006 studies were designed after review and analysis of the data from the 003A/B studies. As a result of this review, a number of modifications were made to the design of the 005/006 protocol, as compared to the 003A/B studies, A summary of the modifications made that may have contributed to the observed difference in outcome of the primary endpoints is provided in Table 6.

Impact of Dose and Dose Regimen

Facial Rhytids and Nasolabial Folds The selected dose for the treatment of nasolabial folds (up to 2 mL of $1.0$-$2.0 \times 10^7$ cells/mL, administered at 0.1 mL per linear centimeter) is based not only data generated in the clinical trials conducted under IND 8641, but also on information gained through commercial use of the fibroblast dosage formulation both in the US and abroad. Study IT-R-001 was a placebo-controlled Phase II dose ranging study that evaluated the fibroblast cell suspension at 0.5, 1.0, and $2.0 \times 10^7$ cells/mL at 0.1 mL per linear centimeter versus placebo for safety and preliminary efficacy in the treatment of facial rhytids. Baseline to four months following the initial injection (primary efficacy timepoint for Study 1T-R-001) in the highest dose group ($2.0 \times 10^7$ cells/mL) gave the best results. Therefore, this was the density of cells that was used in all subsequent studies.

In the 003A/B studies, the dose per linear centimeter was the same as that used in other azficel-T fibroblast dosage formulation studies for this indication (0.1 mL per linear centimeter). However, the total dose for each treatment was limited to 1 mL, over a total treatment area of 10 cm of total. This difference is because Studies 003A/B did not allow for treatment of what is sometimes termed the mesolabial fold wrinkle, which is the fold or wrinkle that extends inferiorly from the corner of the mouth toward the chin. The total dose was increased to 2 mL in 005/006, to permit treatment of the mesolabial fold wrinkle, as it is frequently contiguous with the nasolabial fold wrinkle and is therefore a contributing component to the overall aesthetic outcome. While the total dose permitted was not the only difference between the 003A/B protocol and the 005/006 protocol, this increase in volume of product administered is considered to be a contributing factor in the successful results obtained from the 005/006 studies.

The recommended dose interval of five weeks±one week was determined based on feedback provided by the Investigators from the 003A/B studies and the outcome of the 005/006 trials. The 003A/B investigators advised Isolagen that the time between treatments in those studies (seven to 14 days) was insufficient to permit the inflammation induced by one injection to recede before administration of the next injection. This duration of inflammation was noted only during the injection process and was not reported as an adverse event. When administering sequential injections at the longer intervals permitted by the protocol, investigators reported that the injection sites were more likely to appear closer to normal skin, which led to greater control of both the depth and volume of injection. This led to lengthening the interval between injections in the 005/006 studies first to four, then five±one week. This change is also considered to be a contributing factor in the successful 005/006 study results.

Primary efficacy analysis of the Intent to Treat Population in the 005/006 studies evaluated treatment response between the fibroblast cell suspension and placebo treatment groups as measured by the co-primary efficacy endpoints. For the Evaluator Wrinkle Severity Assessment at Visit 6 (co-primary efficacy endpoint), 26% of IT-randomized subjects versus 7% of placebo-randomized subjects showed a two-point improvement for the bilateral nasolabial fold wrinkles. When only those subjects that actually received at least one treatment with the fibroblast dosage formulation or placebo were included in the analysis (the Modified Intent to Treat (MITT) Population), the percentage of two-point response on the Evaluator Wrinkle Severity Assessment was 30% in IT-treated subjects as compared to 8% for placebo-treated subjects. The one-point response rates in the MITT Population on the Evaluator Wrinkle Severity Assessment were 64% in subjects treated with the fibroblast dosage formulation and 36% in those treated with placebo. Finally, in demonstration of the subtle onset of effect observed with the use of IT, the photographic assessments of efficacy by both the Evaluator and the Subjects showed highly statistically significant difference in treatment response between IT- and placebo-treated subjects. When Evaluator's compared photographs of the subject taken at Baseline side-by-side with photos taken at the final efficacy visit, 57% of IT-treated subjects in the MITT Population and only 20% of placebo-treated subjects in this population were scored as improved. On the subject's photographic assessment (Subject Improvement Assessment), where subjects compared their own Baseline photos to those taken at the final efficacy visit, 67% of IT-treated subjects and 26% of placebo-treated subjects showed improvement. The increase in response rates using this assessment instrument as compared to the live assessment results demonstrates the subtle, gradual onset of effect, which may not be apparent to subjects or evaluators until appearance is compared to baseline.

In summary, for the reasons discussed above, the preferred dosage for the treatment of nasolabial fold wrinkles is to inject one to two mL of the dosage formulation per treatment session, into the superficial papillary dermis of the wrinkles at a dose distribution of 0.1 mL/linear cm, preferably for three treatment sessions separated by five weeks plus or minus seven to ten days.

Figure 4:
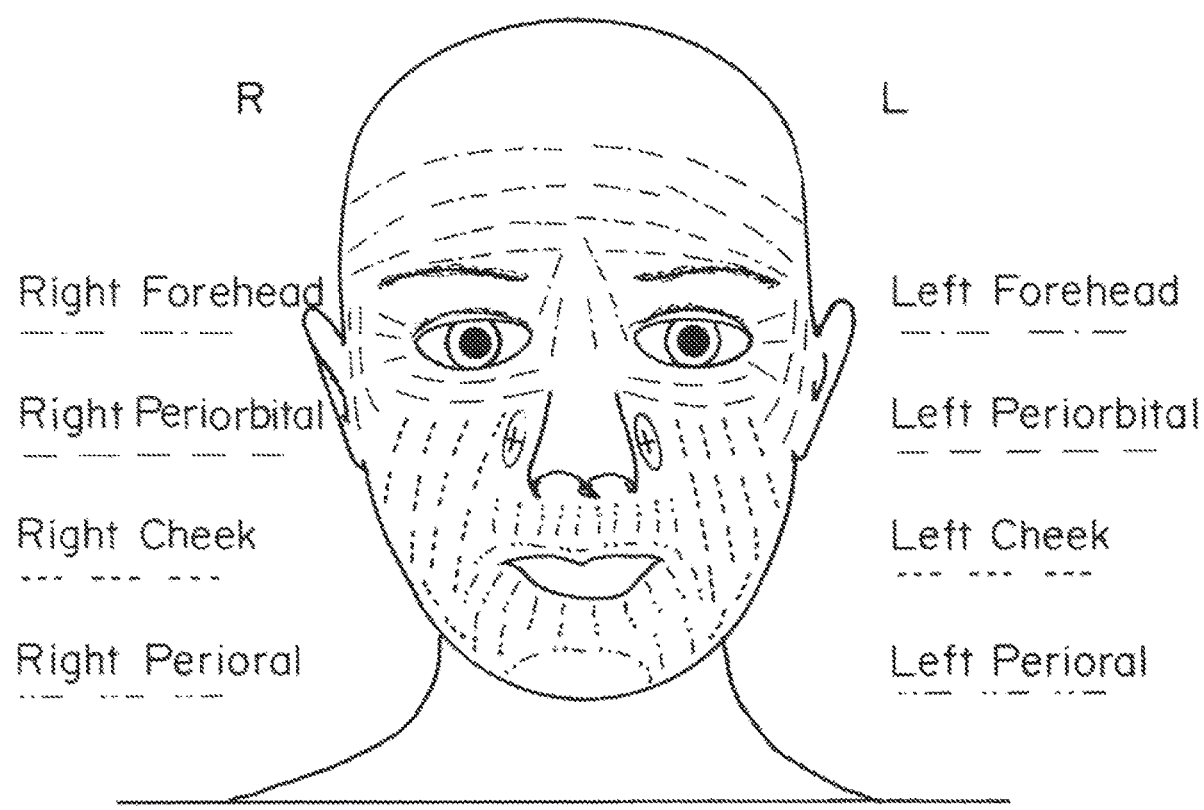
FIG. 4 is a diagram for use in the objective, physician assessed, live grading of acne scarring severity, the "Evaluator Live Acne Scar Assessment Scale," employing the comparative evaluation of relative scarring appearance under direct and tangential lighting

The preferred dosage for the treatment of rhytids in multiple facial regions (i.e. the "full face") is to inject five to six mL of the dosage formulation per treatment session into the superficial papillary dermis according to the treatment map in FIG. 4 at a dose distribution of 0.05 mL/linear cm, preferably for one or two treatment sessions separated by five weeks plus or minus seven to ten days.

Acne Scars

The appropriate dosage for the treatment of acne scars can be determined using a validated method and scale for the objective, physician assessed, live grading of acne scarring severity, the "Evaluator Live Acne Scar Assessment Scale," employing the comparative evaluation of relative scarring appearance under direct and tangential lighting, referring to FIG. 2.

TABLE 1

Evaluator Live Acne Scar Assessment Scale

| Grade | Term | Description |
| --- | --- | --- |
| 0 | Clear | No depressions are seen in the treatment area. Macular discoloration may be seen. |
| 1 | Very Mild | A single depression is easily noticeable with direct lighting (deep). Most or all of the depressions seen are only readily apparent with tangential lighting (shallow). |
| 2 | Mild | A few to several, but less than half of all the depressions are easily noticeable with direct lighting (deep). Most of the depressions seen are only readily apparent with tangential lighting (shallow). |
| 3 | Moderate | More than half of the depressions are apparent with direct lighting (deep). |
| 4 | Severe | All or almost all the lesions can be seen with direct lighting (deep). |

In the study by Layton et al. conducted at the Leeds General Infirmary, the severity of acne scarring was evaluated by lesion counts of atrophic and hypertrophic/keloidal scars. Atrophic scars—defined morphologically as ice-pick, macular atrophic or follicular macular atrophic—translated into scores ranging from 1 to 6 representing 1-5, 6-10, 11-25, 26-50, 51-100 and more than 100 scars, respectively. Ice-pick scars were described as those with an irregular border, jagged edges and sharp margins with steep sides leading to a fibrotic base. Macular atrophic scars were soft and distensible in which the base was often easily creased. Follicular macular atrophic scars were described as small white perifollicular papules or macules. The authors separately quantified keloidal and hypertrophic scars owing to their greater level of disfigurement. Score allocation of 2, 4 and 6 represented one to three, four to seven and more than seven scars of this type, respectively. Keloidal scars were described as those that were indurated and extending beyond the boundaries of the initiating inflammatory acne lesion, while hypertrophic scars were defined as less raised and conforming to the area of the primary acne lesion. A total scar score was then obtained by adding the scores from both atrophic and hypertrophic categories. Such total scores could be calculated separately for the face, chest and back to provide a comprehensive system for scar evaluation, and also provide a means for assessing effective dosage and treatment regimes.

In the preferred embodiment, acne scars are treated by injecting two to twelve mL of the fibroblast dosage formulation per treatment session, into the superficial papillary dermis at a dose distribution of 0.1 mL/cm$^2$ of scarred area, for one to three treatment sessions separated by fourteen days plus or minus three days.

Burns

A potentially serious long-term consequence of burn injuries to the deep dermis are post-injury scars. The formation of restrictive scars due to serious burns can prevent the normal movements of the affected area and restrict range of motion (flexion, adduction, and/or extension). In fact, "burn scarring and contracture affecting function remain the most frustrating late complications of burn injury" (Iwuagwu, Plast Reconstr Surg. 1999 April; 103(4):1198-204). These scars can have a significantly negative impact on quality of life by causing pain and reduced functionality. Depending on their location, restrictive burn scars may result in significant impairment and loss of function of the upper extremity. The fibroblast dosage formulation is particularly useful in the treatment of restrictive burn scars to the upper extremities, specifically to reduce the level of impairment and associated disability experienced by the subject.

The preferred dosage for the treatment of restrictive burn scars is to inject one to ten mL of the dosage formulation per treatment session into the palpated restriction band of the burn scar at a dose distribution of 0.1-0.5 mL/cm$^2$ of scarred area, preferably for one to five treatments separated by two to six weeks.

Case reports from the UK, where the previously available fibroblast formulation was available, demonstrated success for burn scars and wounds with no adverse effects.

Dr. Chris Inglefield in London reported a case of a man with multiple burns to neck, lower face, parts of his eyes and ears. The subject previously had received a fibroblast formulation for facial rhytids and therefore had cells in storage at the time of his burn. This enabled him to have his facial burns treated within six weeks of his initial injury. He subsequently received three additional treatments three months after the injuries. Each treatment was performed under topical anesthesia and comprised of 3-4 ml of cells given in 30-40 injections. The subject previously had been treated with skin grafts. The subject reported improved movement of his face and neck and improved texture and pliability of his skin within three weeks of the first treatment.

Dr. W. Gregory Chernoff at Indiana University has also used a fibroblast formulation in ten non-healing laser burn wounds. Despite the fact that these wounds had not healed for periods of three to nine months prior to treatment with fibroblasts, he noted complete healing six weeks after final injection of the cells (Boss, et al. 2000 Clinical Plastic Surgery 27:613-626).

In the US, two burn victims have benefited from compassionate use of fibroblast formulations with great improvement in their non-healing burn wounds. A victim of the Oklahoma City Bombing was tragically scarred from the explosion. After months of surgery, laser resurfacing and other treatments both to save her life and improve her appearance, she was treated with fibroblasts to help with failed skin grafts and other non-healing wounds she still bore on her face and neck. The non-healing wounds closed and healed after treatment. In addition she had noted improvement in the appearance of her scars.

Another subject with 12 non-healing wounds on her forehead and mallar region from a burn from a laser was treated with a fibroblast formulation on a compassionate use basis. Her only alternative at the time she was treated was a bovine skin graft. Following treatment, most of the wounds healed within six weeks of injection.

The following case reports indicate that fibroblast formulations can improve not just sub-acute or healing burn wounds, but also longstanding, well healed but debilitating restrictive burn scars.

Dr. Chris Inglefield in London, UK reported the case of a woman who had sustained multiple burns two years prior to presentation, resulting in major facial scars that restricted her facial expression on her left side. The subject's injury had severe negative psychological consequences and she felt that she had "lost who she was". The subject received three treatments to her face of 3 mL each. Within six to eight weeks the subject, her family and the treating physician noted remarkable improvement, such that her mother felt that her old daughter "was back". Her ability to move her face improved as did the skin texture and appearance. The same subject then underwent therapy for contracted scars and non-healing wounds on her hands. Prior to therapy the subject was having difficulty manipulating small objects in her jewelry making course. Within four weeks after treatment the wounds had healed and she had improved ability to perform her jewelry making tasks.

Dr. Mark Palmer in Leeds, UK reported on another subject treated for chronic wounds of 10 years duration to her neck, shoulders and upper arms. Prior to treatment the subject had severely restricted range of motion of her neck and shoulder and required daily opiate analgesia for her chronic pain. The subject received a total of two four mL treatments in her neck region. Even after the first treatment the subject reported improved range of motion and skin texture. By the second treatment the subject's range of motion was near normal and a dramatic change in scar appearance and texture was noted.

The same subject subsequently underwent treatment of her upper arm scars. Prior to treatment these scars had been severely disabling, such that she was unable to lift her arm beyond 90° due to pain. By three months after a single treatment of 1.5 mL each to two contracted scar bands on her arm, the scars had almost disappeared and the subject had restored 180° range of motion without pain.

Modifications and variations of the compositions and methods of manufacture and use will be apparent to those skilled in the art from the foregoing detailed description and are intended to come within the scope of the appended claims. All cited references are specifically incorporated by reference.

I claim:

1. A method of treating skin defects, the method comprising the steps of:
   a) determining a total cell count of an in vitro expanded autologous human fibroblast population of between $3.4 \times 10^8$ and $1 \times 10^9$ cells;
   b) freezing a sample of the cell population of step (a) in a cryopreservation medium comprising a cryopreservative, Iscove's Modified Dulbecco's Medium (IMDM), and dimethyl sulfoxide (DMSO) via a controlled rate freezing step process,
   wherein the freezing process comprises of a control rate freezing step to the following ramp program:
   STEP 1: wait at 4.0 C
   STEP 2: 1.0° C./minC/m to −4.0° C. (sample probe)
   STEP 3: 25.0° C./minC/m to −40° C. (chamber probe)
   STEP 4: 10.0° C./minC/m to −12.0° C. (chamber probe)
   STEP 5: 1.0° C./minC/m to −40° C. (chamber probe)
   STEP 6: 10.0° C./minC/m to −90° C. (chamber probe)
   STEP 7: end;
   c) thawing a frozen sample of the autologous human fibroblast cell population from step (b);
   d) determining that the thawed sample of cells of step (c) comprise at least 98% autologous human fibroblasts;
   e) determining that at least 85% of the thawed cells of step (c) are viable after freezing and thawing to render a cell formulation, wherein cell viability is determined using a membrane-permeable dye and a membrane-impermeable dye combination; and
   f) injecting an effective amount of a frozen and thawed dosage formulation consisting essentially of between 1.0 and $2.7 \times 10^7$ cells/mL of the thawed cells of (c) into the superficial papillary dermis of a site to be treated, in two or three treatments separated by five weeks plus or minus seven to ten days,
   wherein at least 98% of the thawed cells are autologous human fibroblast cells reactive with a cell surface marker for fibroblasts and not with a cell surface marker for keratinocyte cells, and at least 85% of which are viable after freezing and thawing,
   wherein two to six mLs of the dosage formulation is injected in each treatment, and
   wherein the dosage formulation does not comprise a structural filler and acts gradually to treat skin defects over time through tissue repair and regeneration.

2. The method of claim 1 for the treatment of rhytids, nasolabial and melolabial folds, perioral lines, lateral canthal lines, periorbital lines, and glabellar lines.

3. The method of claim 1 comprising injecting the dosage formulation at between 0.05 and 0.5 mL per linear centimeter.

4. The method of claim 1 for the treatment of nasolabial fold wrinkles comprising administering one to two mL of the dosage formulation per treatment session, injected into the superficial papillary dermis of the wrinkles at a dose distribution of 0.1 mL/linear cm, for three treatment sessions separated by five weeks plus or minus seven to ten days.

5. The method of claim 1 for the treatment of rhytids in multiple facial regions comprising injecting five to six mL per treatment session, into the superficial papillary dermis at a dose distribution of 0.05 mL/linear cm, for one or two treatment sessions separated by five weeks plus or minus seven to ten days.

6. The method of claim 1 for the treatment of acne scars comprising injecting two to twelve mL per treatment session, into the superficial papillary dermis at a dose distribution of 0.1 mL/cm$^2$ of scarred area, for one to three treatment sessions separated by fourteen days plus or minus three days.

7. The method of claim 1 for the treatment of restrictive burn scars, comprising injecting one to ten mL per treatment session, into the palpated restriction band of the burn scar at a dose distribution of 0.1-0.5 mL/cm$^2$ of scarred area, for one to five treatments separated by two to six weeks.

* * * * *